(12) United States Patent
Blommel et al.

(10) Patent No.: US 10,155,704 B2
(45) Date of Patent: Dec. 18, 2018

(54) PROCESSES AND APPARATUSES FOR PRODUCTION OF BUTADIENE

(71) Applicants: UOP LLC, Des Plaines, IL (US); TPC Group, LLC, Houston, TX (US)

(72) Inventors: Jeannie Mee Blommel, Oregon, WI (US); Charles P. Luebke, Mount Prospect, IL (US); Clifford A. Maat, Pearland, TX (US)

(73) Assignees: UOP LLC, Des Plaines, IL (US); TPC Group, LLC, Houston, TX (US)

( * ) Notice: Subject to any disclaimer, the term of this patent is extended or adjusted under 35 U.S.C. 154(b) by 0 days.

(21) Appl. No.: 15/789,934

(22) Filed: Oct. 20, 2017

(65) Prior Publication Data

US 2018/0037523 A1 Feb. 8, 2018

Related U.S. Application Data

(63) Continuation of application No. PCT/US2016/053547, filed on Sep. 23, 2016.

(Continued)

(51) Int. Cl.
*C07C 5/48* (2006.01)
*C07C 7/11* (2006.01)

(Continued)

(52) U.S. Cl.
CPC ............ *C07C 5/48* (2013.01); *C07C 7/005* (2013.01); *C07C 7/09* (2013.01); *C07C 7/11* (2013.01); *C07C 2523/745* (2013.01)

(58) Field of Classification Search
CPC .. C07C 5/48; C07C 7/005; C07C 7/09; C07C 7/11; C07C 2523/745; C07C 11/167
See application file for complete search history.

(56) References Cited

U.S. PATENT DOCUMENTS

| 4,595,788 A | 6/1986 | Yamamoto et al. |
| 2015/0080627 A1* | 3/2015 | Caciula ............... C07C 5/09 585/315 |

FOREIGN PATENT DOCUMENTS

| CN | 202516539 U | 11/2012 |
| CN | 103086829 A | 5/2013 |

(Continued)

OTHER PUBLICATIONS

International Search report for PCT/US2016/053547, dated Dec. 29, 2016.

*Primary Examiner* — Brian A McCaig
*Assistant Examiner* — Jason Y Chong
(74) *Attorney, Agent, or Firm* — Greer, Burns & Crain, Ltd.

(57) ABSTRACT

Processes and apparatuses for the production of butadienes are provided. In an embodiment, a process for production of butadienes includes passing a reactor feed stream comprising a hydrocarbon stream comprising butene, a steam stream and a oxygen rich stream to a dehydrogenation reactor. The reactor feed stream is oxidatively dehydrogenated in the dehydrogenation reactor in presence of an oxidative dehydrogenation catalyst to provide an effluent stream comprising butadiene. The effluent stream is cooled in a quench tower to provide a cooled effluent stream and a bottoms water stream. The cooled effluent stream is passed to an aldehyde scrubber to provide a scrubbed effluent stream and a spent water stream comprising aldehydes. A first portion of the bottoms water stream is passed from the quench tower to the aldehyde scrubber.

17 Claims, 1 Drawing Sheet

Related U.S. Application Data

(60) Provisional application No. 62/232,751, filed on Sep. 25, 2015.

(51) Int. Cl.
*C07C 7/00* (2006.01)
*C07C 7/09* (2006.01)

(56) References Cited

FOREIGN PATENT DOCUMENTS

| | | |
|---|---|---|
| GB | 779629 A | 7/1957 |
| JP | 2012077076 A | 10/2013 |
| JP | 2013213028 A | 10/2013 |
| WO | 2012157495 A1 | 11/2012 |

* cited by examiner

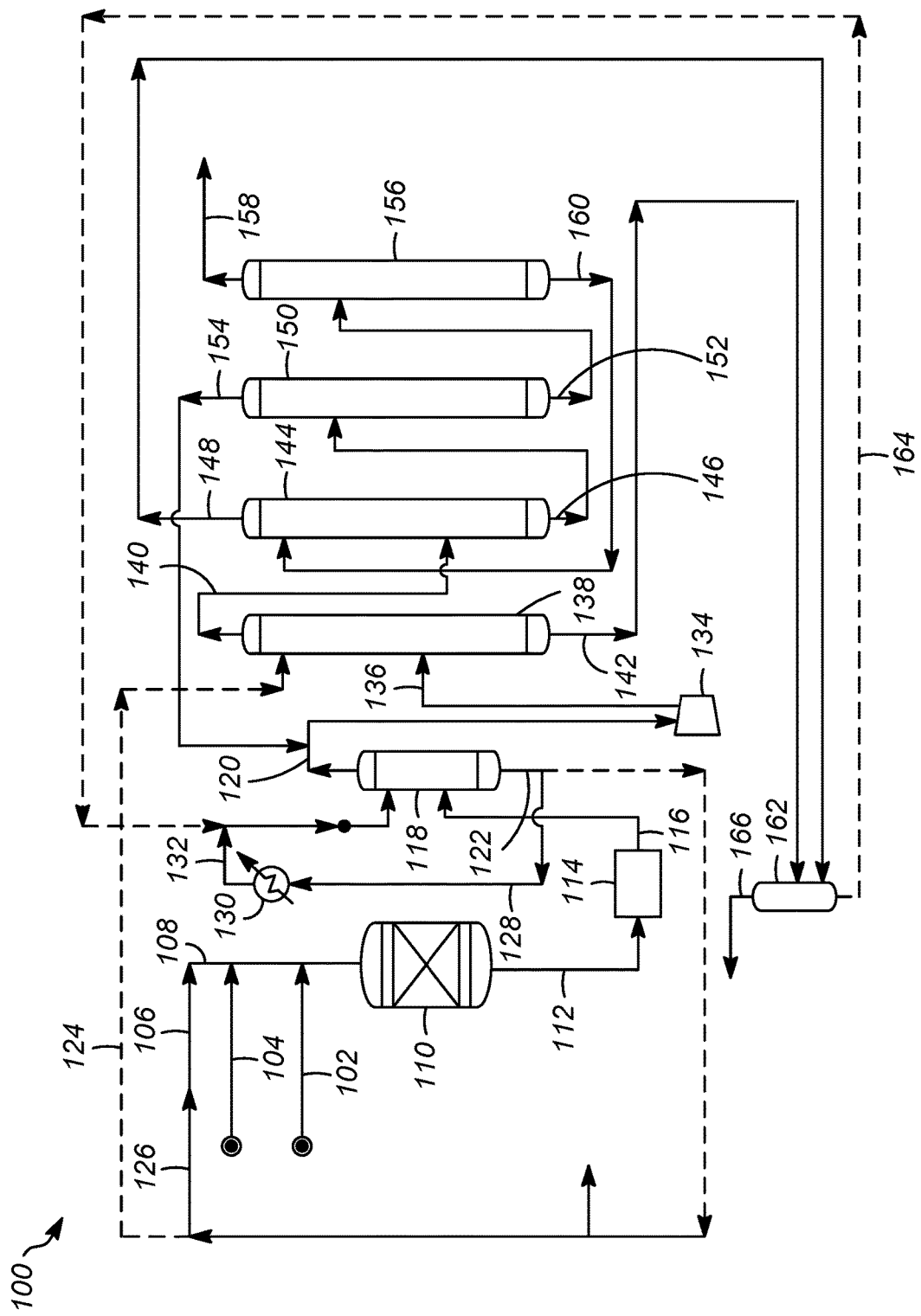

PROCESSES AND APPARATUSES FOR PRODUCTION OF BUTADIENE

CROSS-REFERENCE TO RELATED APPLICATIONS

This application is a Continuation of copending International Application No. PCT/US2016/053547 filed Sep. 23, 2016 which application claims benefit of U.S. Provisional Application No. 62/232,751 filed Sep. 25, 2015, now expired, the contents of which cited applications are hereby incorporated by reference in their entirety.

TECHNICAL FIELD

The technical field generally relates to a process for the production of butadiene. More particularly, the technical field relates to processes and apparatuses for the integration of a butadiene recovery process in an oxidative dehydrogenation process.

BACKGROUND

The use of plastics and rubbers are widespread in today's world. The production of these plastics and rubbers are from the polymerization of monomers which are generally produced from petroleum. The monomers are generated by the breakdown of larger molecules to smaller molecules which can be modified. The monomers are then reacted to generate larger molecules comprising chains of the monomers. An important example of these monomers is light olefins, including ethylene and propylene, which represent a large portion of the worldwide demand in the petrochemical industry. Light olefins, and other monomers, are used in the production of numerous chemical products via polymerization, oligomerization, alkylation and other well-known chemical reactions. Producing large quantities of light olefin material in an economical manner, therefore, is a focus in the petrochemical industry. These monomers are essential building blocks for the modern petrochemical and chemical industries. The main source for these materials in present day refining is the steam cracking of petroleum feeds.

Another important monomer is 1,3-butadiene. Butadiene is a basic chemical component for the production of a range of synthetic rubbers and polymers, as well as the production of precursor chemicals for the production of other polymers. Examples include homopolymerized products such as polybutadiene rubber (PBR), or copolymerized butadiene with other monomers, such as styrene and acrylonitrile. Butadiene is also used in the production of resins such as acrylonitrile butadiene styrene.

Butadiene is typically recovered as a byproduct from the cracking process, wherein the cracking process produces light olefins such as ethylene and propylene. With the increase in demand for rubbers and polymers having the desired properties of these rubbers, an aim to improving butadiene yields from materials in a petrochemical plant will improve the plant economics. The economics of butadiene production can be strongly affected by capital and operating costs.

The TPC/UOP Oxo-D Process is a process that can convert n-butenes to butadiene. There is a very large water circulation requirement in the system to provide circulating water to the reactor section, quench tower and aldehyde removal section. With these three large water circulation loops, there is a significant utility penalty to the process.

Accordingly, it is desirable to provide apparatuses and processes which results in a better integration of water circulation loops in the Oxo-D Process and provide a reduction in the overall utilities and operating costs. Furthermore, other desirable features and characteristics of the present subject matter will become apparent from the subsequent detailed description of the subject matter and the appended claims, taken in conjunction with the accompanying drawing and this background of the subject matter.

BRIEF SUMMARY

Various embodiments contemplated herein relate to processes and apparatuses for production of butadienes. The exemplary embodiments taught herein provide efficient integration of water circulation loops in the On-Purpose Butadiene Process.

In accordance with an exemplary embodiment, a process is provided for the production of butadienes. The process includes passing a reactor feed stream comprising a hydrocarbon stream comprising butene, a steam stream and a oxygen rich stream to a dehydrogenation reactor. The reactor feed stream is oxidatively dehydrogenated in the dehydrogenation reactor in presence of an oxidative dehydrogenation catalyst to provide an effluent stream comprising butadiene. The effluent stream is cooled in a quench tower to provide a cooled effluent stream and a bottoms water stream. The cooled effluent stream is passed to an aldehyde scrubber to provide a scrubbed effluent stream and a spent water stream comprising aldehydes. A first portion of the bottoms water stream is passed from the quench tower to the aldehyde scrubber.

In accordance with another exemplary embodiment, a process is provided for the production of butadienes. The process includes passing a reactor feed stream comprising a hydrocarbon stream comprising butene, a steam stream and a oxygen rich stream to a dehydrogenation reactor. The reactor feed stream is oxidatively dehydrogenated in the dehydrogenation reactor in presence of an oxidative dehydrogenation catalyst to provide an effluent stream comprising butadiene. The effluent stream is cooled in a quench tower to provide a cooled effluent stream and a bottoms water stream. The cooled effluent stream is passed to an oxygenate scrubber to provide a spent water stream comprising oxygenates and a scrubbed effluent stream. A first portion of the bottoms water stream is passed from the quench tower to the oxygenate scrubber. A second portion of the bottoms water stream is passed from the quench tower to the dehydrogenation reactor. The scrubbed effluent stream and an absorption oil stream is passed to an absorber column to provide an overhead absorber stream comprising light gases and an absorption oil stream comprising C4's. The absorption oil stream comprising C4's is passed to a degasser column to provide a degassed absorption oil stream. The degassed absorption oil stream is passed to a C4 stripper column to strip butadiene and C4's from the absorption oil to provide a crude butadiene product stream and the absorption oil stream. The spent water stream and the overhead absorber stream are passed to an aldehyde stripper column to provide a gas stream comprising oxygenates and a stripped bottoms water stream.

In accordance with yet another exemplary embodiment, an apparatus is provided for the production of butadienes. The apparatus includes a dehydrogenation reactor oxidatively dehydrogenating a reactor feed stream comprising a hydrocarbon stream comprising butene, a steam stream and a oxygen rich stream in presence of a oxidative dehydrogenation catalyst to provide an effluent stream comprising butadiene. A quench tower in fluid communication with the dehydrogenation reactor to provide a cooled effluent stream and a bottoms water stream. An aldehyde scrubber in fluid communication with the quench tower to provide a scrubbed effluent stream and a spent water stream comprising aldehydes. An absorber column in fluid communication with the aldehyde scrubber to provide an overhead absorber stream comprising light gases and an absorption oil stream comprising C4's. A degasser column in fluid communication with the absorber column to provide a degassed absorption oil stream. A C4 stripper column is in fluid communication with the degasser column to provide a crude butadiene product stream and the absorption oil. An aldehyde stripper column in downstream communication with the absorber column through an overhead absorber line and is in downstream communication with the aldehyde scrubber through a spent water stream line to provide a stripped bottoms water stream; wherein the aldehyde scrubber is in downstream communication with the quench tower through a first line comprising a first portion of the bottoms water stream and the dehydrogenation reactor is in downstream communication with the quench tower through a second line comprising a second portion of the bottoms water stream.

BRIEF DESCRIPTION OF THE DRAWING

The FIGURE is a schematic diagram of a process and an apparatus for the production of butadiene in accordance with an exemplary embodiment.

DEFINITIONS

As used herein, the term "stream" can include various hydrocarbon molecules and other substances.

The notation "$C_x$" means hydrocarbon molecules that have "x" number of carbon atoms, $C_x^+$ means hydrocarbon molecules that have "x" and/or more than "x" number of carbon atoms, and $C_x^-$ means hydrocarbon molecules that have "x" and/or less than "x" number of carbon atoms.

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and nonaromatic hydrocarbons. Moreover, the hydrocarbon molecules may be abbreviated C1, C2, C3 . . . Cn where "n" represents the number of carbon atoms in the one or more hydrocarbon molecules. Furthermore, a superscript "+" or "−" may be used with an abbreviated one or more hydrocarbons notation, e.g., C3+ or C3−, which is inclusive of the abbreviated one or more hydrocarbons. As an example, the abbreviation "C3+" means one or more hydrocarbon molecules of three carbon atoms and/or more. Also, the term "stream" can include or consist of other fluids, such as a hydrogen.

As used herein, the term "overhead stream" can mean a stream withdrawn at or near a top of a vessel, such as a column.

As used herein, the term "bottom stream" can mean a stream withdrawn at or near a bottom of a vessel, such as a column.

As depicted, process flow lines in the FIGURE can be referred to interchangeably as, e.g., lines, pipes, feeds, gases, products, discharges, parts, portions, or streams.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

The term "predominantly" means a majority, suitably at least 80 wt % and preferably at least 90 wt %.

The term "passing" includes "feeding" and means that the material passes from a conduit or vessel to an object.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description. It will be appreciated by one skilled in the art that various features of the above described process, such as pumps, instrumentation, heat-exchange and recovery units, condensers, compressors, flash drums, feed tanks, and other ancillary or miscellaneous process equipment that are traditionally used in commercial embodiments of hydrocarbon conversion processes have not been described or illustrated. It will be understood that such accompanying equipment may be utilized in commercial embodiments of the flow schemes as described herein. Such ancillary or miscellaneous process equipment can be obtained and designed by one skilled in the art without undue experimentation.

An embodiment of a process for the production of butadiene is addressed with reference to a process and apparatus 100 providing efficient integration of water circulation loops in the production of butadiene as shown in the FIGURE. The apparatus and method 100 includes an oxidative dehydrogenation reactor 110, a heat recovery unit 114, a quench tower 118, a compressor 134, an oxygenate scrubber 138, an absorber column 144, a degasser column 150, a C4 stripper column 156 and an aldehyde stripper column 162.

In accordance with the process and as shown in the FIGURE, a hydrocarbon feed comprising butene 102, an oxygen rich stream 104 and a steam stream 106 are passed to the oxidative dehydrogenation reactor 110. In accordance with an exemplary embodiment as shown, the hydrocarbon feed 102, the oxygen rich stream 104 and the steam stream 106 combine to form a reactor feed stream 108. Subsequently, the reactor feed stream 108 is passed to the oxidative dehydrogenation reactor 110. The reactor feed stream 108 is oxidatively dehydrogenated in the dehydrogenation reactor 110 in presence of an oxidative dehydrogenation catalyst to provide an effluent stream 112 comprising butadiene. In accordance with an exemplary embodiment, the oxidative dehydrogenation catalyst is a ferritic oxidative dehydrogenation catalyst. The effluent steam 112 is passed to the heat recovery unit 114 for recovering available heat and provide a heat recovered stream 116. Subsequently, the heat recovered stream 116 is passed to the quench tower 118. The heat recovered stream 116 is cooled in the quench tower 118 to provide a cooled effluent stream 120 and a bottoms water stream 122. The cooled effluent stream 120 is passed to a compressor 134 to generate a compressed intermediate product stream 136. The compressed intermediate product stream 136 is passed to the oxygenate scrubber 138. In various embodiments of the instant invention, the oxygenate scrubber 138 is an aldehyde scrubber 138. In accordance with an exemplary embodiment, the aldehyde scrubber 138 does not require a reboiler or condenser.

A first line 124 comprising a first portion of the bottoms water stream 122 is passed to the aldehyde scrubber 138. In accordance with an exemplary embodiment, the aldehyde scrubber 138 is in direct and downstream communication with the bottoms of the quench tower 118 through the first line 124 comprising the first portion. A second line 126 comprising a second portion of the bottoms water stream 122 is passed to the dehydrogenation reactor 110. In accordance with an exemplary embodiment, the second portion of the bottoms water stream 122 is passed to a steam generator (not shown) to generate stream before being passed to the dehydrogenation reactor 110. In one example, the dehydrogenation reactor 110 is in direct and downstream communication with the bottoms of the quench tower 118 through the second line 126. A third line 128 comprising a third portion of the bottoms water stream 122 is passed through a cooler 130 to provide a cooled stream 132 which is subsequently recycled back to the quench tower 118.

Referring back to the aldehyde scrubber 138, a scrubbed effluent stream 140 and a spent water stream 142 comprising aldehydes is obtained from the aldehyde scrubber 138. Subsequently, the scrubbed effluent stream 140 is passed to the absorber column 144. In the absorber column 144, C4's including butadiene present in the scrubbed effluent stream 140 are absorbed in presence of an absorption oil and lighter gases are separated. In accordance with an exemplary embodiment, the absorption oil is selected from the group consisting of naphtha, toluene, xylenes, styrene and naphthalenes. In accordance with one exemplary embodiment, the absorber column 144 does not require a reboiler or condenser. An absorption oil stream 146 comprising C4's and an overhead absorber stream 148 comprising light gases is withdrawn from the absorber column 144. The absorption oil stream 146 is passed to the degasser column 150 to remove non-C4 volatiles in a degasser overhead stream 154. In accordance with an exemplary embodiment, the degasser column 150 has a reboiler but not require a condenser. The degasser overhead stream 154 is subsequently mixed with cooled effluent stream 120 prior to being passed to the compressor 134. A degassed absorption oil stream 152 is withdrawn from the degasser column 150 and passed to a C4 stripper column 156 to strip butadiene and C4's from the absorption oil to provide a crude butadiene product stream 158 which is sent for further purification to obtain butadiene product. Further, an absorption oil stream 160 is recovered from the bottom of the C4 stripper column 156 and is recycled to the absorber column 144 as shown.

Referring back to the aldehyde scrubber 138 and the absorber column 144, the spent water stream 142 from the bottom of the aldehyde scrubber 138 and the overhead absorber stream 148 from the top of the absorber column 144 are passed to an aldehyde stripper column 162. Light gases present in the overhead absorber stream 148 are used as a stripping medium to strip aldehydes present in the spent water stream 142. A stripped bottoms water stream 164 is recovered from the bottoms of the aldehyde stripper column 162 and is passed to the quench tower 118 as shown. Further, a gas stream 166 comprising oxygenates is withdrawn from the top of the aldehyde stripper column 162.

In accordance with the instant process flow scheme as discussed above, applicants have found that the aldehyde content of the bottoms water stream 122 from the quench tower 118 is low enough that the bottoms of the quench tower can be used directly in the dehydrogenation reactor 110 and the aldehyde scrubber 138 as discussed above. The instant arrangement helps in reducing the size of the aldehyde stripper column 162 as only bottoms of the aldehyde scrubber 138 is being sent to the aldehyde stripper column 162. Moreover, applicants' have found that using the overhead absorber stream 148 comprising light gases for stripping the aldehydes present in the spent water stream 142 provides an advantage over the conventional method as there is no reboiler or condenser required in the aldehyde stripper column 162. Further, the stripped bottoms water stream 164 is cold and can be used directly as quench in the quench tower 118 and results in reduced cooling requirement of the quench water circulation system.

Specific Embodiments

While the following is described in conjunction with specific embodiments, it will be understood that this description is intended to illustrate and not limit the scope of the preceding description and the appended claims.

A first embodiment of the invention is a process for the production of butadienes comprising a) passing a reactor feed stream comprising a hydrocarbon stream comprising butene, a steam stream and a oxygen rich stream to a dehydrogenation reactor; b) oxidatively dehydrogenating the reactor feed stream in the dehydrogenation reactor in presence of an oxidative dehydrogenation catalyst to provide an effluent stream comprising butadiene; c) cooling the effluent stream in a quench tower to provide a cooled effluent stream and a bottoms water stream; d) passing the cooled effluent stream to an aldehyde scrubber to provide a scrubbed effluent stream and a spent water stream comprising aldehydes; and e) passing a first portion of the bottoms water stream from the quench tower to the aldehyde scrubber. An embodiment of the invention is one, any or all of prior embodiments in this paragraph up through the first embodiment in this paragraph further comprising passing the scrubbed effluent stream and an absorption oil stream to the absorber column, wherein C4's including butadiene in the scrubbed effluent stream are absorbed in the absorption oil and an overhead absorber stream comprising light gases is separated. An embodiment of the invention is one, any or all of prior embodiments in this paragraph up through the first embodiment in this paragraph further comprising passing the absorption oil comprising the C4's through a degasser column to provide a degasser overhead stream comprising non-C4 volatiles and a degassed absorption oil stream. An embodiment of the invention is one, any or all of prior embodiments in this paragraph up through the first embodiment in this paragraph further comprising passing the degassed absorption oil stream to a C4 stripper column to strip butadiene and C4's from the degassed absorption oil to provide a crude butadiene product stream and the absorption oil stream. An embodiment of the invention is one, any or all of prior embodiments in this paragraph up through the first embodiment in this paragraph further comprising recycling the absorption oil stream from a bottom of the C4 stripper column to the absorber column. An embodiment of the invention is one, any or all of prior embodiments in this paragraph up through the first embodiment in this paragraph further comprising passing the spent water from the aldehyde scrubber and passing the overhead absorber stream to the aldehyde stripper column to provide a stripped bottoms water stream. An embodiment of the invention is one, any or all of prior embodiments in this paragraph up through the first embodiment in this paragraph further comprising passing at least a portion of the stripped bottoms water stream to the quench tower. An embodiment of the invention is one, any or all of prior embodiments in this paragraph up through the first embodiment in this paragraph further comprising passing the degassed overhead gas to the cooled effluent stream prior to passing the cooled effluent stream through the aldehyde scrubber. An embodiment of the invention is one, any or all of prior embodiments in this paragraph up through the first embodiment in this paragraph further comprising passing a second portion of the bottoms water stream from the quench tower to the dehydrogenation reactor An embodiment of the invention is one, any or all of prior embodiments in this paragraph up through the first embodiment in this paragraph, wherein the second portion of the bottoms water stream is converted to steam before passing to the dehydrogenation reactor. An embodiment of the invention is one, any or all of prior embodiments in this paragraph up through the first embodiment in this paragraph, wherein the oxidative dehydrogenation catalyst is a ferritic oxidative dehydrogenation catalyst. An embodiment of the invention is one, any or all of prior embodiments in this paragraph up through the first embodiment in this paragraph, wherein the absorber oil comprises one or more compounds selected from the group consisting of naphtha, toluene, xylenes, styrene and naphthalenes.

A second embodiment of the invention is a process for the production of butadienes comprising a) passing a reactor feed stream comprising a hydrocarbon stream comprising butene, a steam stream and a oxygen rich stream to a dehydrogenation reactor; b) oxidatively dehydrogenating the reactor feed stream in the dehydrogenation reactor in presence of an oxidative dehydrogenation catalyst to provide an effluent stream comprising butadiene; c) cooling the effluent stream in a quench tower to provide a cooled effluent stream and a bottoms water stream; d) passing the cooled effluent stream to an oxygenate scrubber to provide a spent water stream comprising oxygenates and a scrubbed effluent stream; e) passing a first portion of the bottoms water stream from the quench tower to the oxygenate scrubber; f) passing a second portion of the bottoms water stream from the quench tower to the dehydrogenation reactor; g) passing the scrubbed effluent stream and an absorption oil stream to an absorber column to provide an overhead absorber stream comprising light gases and an absorption oil stream comprising C4's; h) passing the absorption oil stream comprising C4's to a degasser column to provide a degassed absorption oil stream; and i) passing the degassed absorption oil stream to a C4 stripper column to strip butadiene and C4's from the absorption oil to provide a crude butadiene product stream and the absorption oil stream; and j) passing the spent water stream and the overhead absorber stream to an aldehyde stripper column to provide a gas stream comprising oxygenates and a stripped bottoms water stream. An embodiment of the invention is one, any or all of prior embodiments in this paragraph up through the second embodiment in this paragraph further comprising passing at least a portion of the stripped bottoms water stream to the quench tower. An embodiment of the invention is one, any or all of prior embodiments in this paragraph up through the second embodiment in this paragraph further comprising passing the absorption oil stream from a bottom of the C4 stripper column to the absorber column. An embodiment of the invention is one, any or all of prior embodiments in this paragraph up through the second embodiment in this paragraph, wherein the second portion of the bottoms water stream is passed to a steam generator to generate steam before being passed to the dehydrogenation reactor. An embodiment of the invention is one, any or all of prior embodiments in this paragraph up through the second embodiment in this paragraph, wherein the oxygenate scrubber is an aldehyde scrubber and the spent water comprises aldehydes.

A third embodiment of the invention is an apparatus for the production of butadienes comprising a) a dehydrogenation reactor oxidatively dehydrogenating a reactor feed stream comprising a hydrocarbon stream comprising butene, a steam stream and a oxygen rich stream in presence of a oxidative dehydrogenation catalyst to provide an effluent stream comprising butadiene; b) a quench tower in fluid communication with the dehydrogenation reactor to provide a cooled effluent stream and a bottoms water stream; c) an aldehyde scrubber in fluid communication with the quench tower to provide a scrubbed effluent stream and a spent water stream comprising aldehydes; d) an absorber column in fluid communication with the aldehyde scrubber to provide an overhead absorber stream comprising light gases and an absorption oil stream comprising C4's. e) a degasser column in fluid communication with the absorber column to provide a degassed absorption oil stream; f) a C4 stripper column in fluid communication with the degasser column to provide a crude butadiene product stream and the absorption oil; g) an aldehyde stripper column in downstream communication with the absorber column through an overhead absorber line and is in downstream communication with the aldehyde scrubber through a spent water stream line to provide a stripped bottoms water stream; wherein the aldehyde scrubber is in downstream communication with the quench tower through a first line comprising a first portion of the bottoms water stream and the dehydrogenation reactor is in downstream communication with the quench tower through a second line comprising a second portion of the bottoms water stream. An embodiment of the invention is one, any or all of prior embodiments in this paragraph up through the third embodiment in this paragraph, wherein the quench tower is in downstream communication with the aldehyde stripper column through a stripped bottoms water stream line. An embodiment of the invention is one, any or all of prior embodiments in this paragraph up through the third embodiment in this paragraph further comprising a steam generator in downstream communication with the second line from the quench tower and the dehydrogenation reactor is in downstream communication with the steam generator.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

The invention claimed is:

1. A process for the production of butadienes comprising:
   a) passing a reactor feed stream comprising a hydrocarbon stream comprising butene, a steam stream and a oxygen rich stream to a dehydrogenation reactor;
   b) oxidatively dehydrogenating the reactor feed stream in the dehydrogenation reactor in presence of an oxidative dehydrogenation catalyst to provide an effluent stream comprising butadiene;
   c) cooling the effluent stream in a quench tower to provide a cooled effluent stream and a bottoms water stream;
   d) passing the cooled effluent stream to an aldehyde scrubber to provide a scrubbed effluent stream and a spent water stream comprising aldehydes; and
   e) passing a first portion of the bottoms water stream from the quench tower to the aldehyde scrubber.

2. The process of claim 1 further comprising passing the scrubbed effluent stream and an absorption oil stream to an absorber column, wherein C4's including butadiene in the scrubbed effluent stream are absorbed in the absorption oil and an overhead absorber stream comprising light gases is separated.

3. The process of claim 2 further comprising passing the absorption oil comprising the C4's through a degasser column to provide a degasser overhead stream comprising non-C4 volatiles and a degassed absorption oil stream.

4. The process of claim 3 further comprising passing the degassed absorption oil stream to a C4 stripper column to strip butadiene and C4's from the degassed absorption oil to provide a crude butadiene product stream and the absorption oil stream.

5. The process of claim 4 further comprising recycling the absorption oil stream from a bottom of the C4 stripper column to the absorber column.

6. The process of claim 2 further comprising passing the spent water from the aldehyde scrubber and the overhead absorber stream to the aldehyde stripper column to provide a stripped bottoms water stream.

7. The process of claim 6 further comprising passing at least a portion of the stripped bottoms water stream to the quench tower.

8. The process of claim 3 further comprising passing the degassed overhead gas to the cooled effluent stream prior to passing the cooled effluent stream through the aldehyde scrubber.

9. The process of claim 1 further comprising passing a second portion of the bottoms water stream from the quench tower to the dehydrogenation reactor.

10. The process of claim 9, wherein the second portion of the bottoms water stream is converted to steam before passing to the dehydrogenation reactor.

11. The process of claim 1, wherein the oxidative dehydrogenation catalyst is a ferritic oxidative dehydrogenation catalyst.

12. The process of claim 1, wherein the absorber oil comprises one or more compounds selected from the group consisting of naphtha, toluene, xylenes, styrene and naphthalenes.

13. A process for the production of butadienes comprising:
   a) passing a reactor feed stream comprising a hydrocarbon stream comprising butene, a steam stream and a oxygen rich stream to a dehydrogenation reactor;
   b) oxidatively dehydrogenating the reactor feed stream in the dehydrogenation reactor in presence of an oxidative dehydrogenation catalyst to provide an effluent stream comprising butadiene;
   c) cooling the effluent stream in a quench tower to provide a cooled effluent stream and a bottoms water stream;
   d) passing the cooled effluent stream to an oxygenate scrubber to provide a spent water stream comprising oxygenates and a scrubbed effluent stream;
   e) passing a first portion of the bottoms water stream from the quench tower to the oxygenate scrubber;
   f) passing a second portion of the bottoms water stream from the quench tower to the dehydrogenation reactor;
   g) passing the scrubbed effluent stream and an absorption oil stream to an absorber column to provide an overhead absorber stream comprising light gases and an absorption oil stream comprising C4's;
   h) passing the absorption oil stream comprising C4's to a degasser column to provide a degassed absorption oil stream; and
   i) passing the degassed absorption oil stream to a C4 stripper column to strip butadiene and C4's from the absorption oil to provide a crude butadiene product stream and the absorption oil stream; and
   j) passing the spent water stream and the overhead absorber stream to an aldehyde stripper column to provide a gas stream comprising oxygenates and a stripped bottoms water stream.

14. The process of claim 13 further comprising passing at least a portion of the stripped bottoms water stream to the quench tower.

15. The process of claim 13 further comprising passing the absorption oil stream from a bottom of the C4 stripper column to the absorber column.

16. The process of claim 13, wherein the second portion of the bottoms water stream is passed to a steam generator to generate steam before being passed to the dehydrogenation reactor.

17. The process of claim 13, wherein the oxygenate scrubber is an aldehyde scrubber and the spent water comprises aldehydes.

* * * * *